(12) United States Patent
Kim et al.

(10) Patent No.: US 10,589,121 B2
(45) Date of Patent: Mar. 17, 2020

(54) THERAPY DEVICE FOR EDEMA AND NEUROPATHY

(71) Applicant: COLOR SEVEN CO., LTD., Seoul (KR)

(72) Inventors: Nam Gyun Kim, Seoul (KR); Kyong Jun Park, Seoul (KR)

(73) Assignee: COLOR SEVEN. CO., LTD., Seoul (KR)

( * ) Notice: Subject to any disclaimer, the term of this patent is extended or adjusted under 35 U.S.C. 154(b) by 843 days.

(21) Appl. No.: 14/890,162

(22) PCT Filed: May 13, 2013

(86) PCT No.: PCT/KR2013/004208
§ 371 (c)(1),
(2) Date: Nov. 10, 2015

(87) PCT Pub. No.: WO2014/185558
PCT Pub. Date: Nov. 20, 2014

(65) Prior Publication Data
US 2016/0129281 A1    May 12, 2016

(51) Int. Cl.
*A61N 5/06* (2006.01)
*A61N 5/067* (2006.01)

(52) U.S. Cl.
CPC ......... *A61N 5/0619* (2013.01); *A61N 5/0622* (2013.01); *A61N 2005/067* (2013.01);
(Continued)

(58) Field of Classification Search
CPC ............... A61N 5/0619; A61N 5/0622; A61N 2005/067; A61N 2005/0667;
(Continued)

(56) References Cited

U.S. PATENT DOCUMENTS 5,323,650 A * 6/1994 Fullen ................. A61B 5/1036
340/573.1
6,743,249 B1 * 6/2004 Alden .................. A61N 5/0601
606/1
(Continued)

FOREIGN PATENT DOCUMENTS

JP              11267178 A * 10/1999  .......... G08G 79/025
KR   10-2008-0039971 A       5/2008
(Continued)

OTHER PUBLICATIONS

International Search Report for PCT/KR2013/004208 dated Feb. 7, 2014 from Korean Intellectual Property Office.

*Primary Examiner* — Boniface N Nganga
(74) *Attorney, Agent, or Firm* — Revolution IP, PLLC

(57) ABSTRACT

Disclosed is a therapy device for edema and neuropathy. Colored light within a visible light wavelength range, which is known to be useful for treating edema and neuropathy, is irradiated to a treatment area such as acupuncture points on a foot or a hand, or the surface of the skin, thereby relaxing the smooth muscle tissue of tissue cells with edema or neuropathy, facilitating peripheral vascular circulation and lymphatic circulation, and inducing the secretion of a material for treating edema and neuropathy.

10 Claims, 11 Drawing Sheets

(52) U.S. Cl.
CPC ............. *A61N 2005/0645* (2013.01); *A61N 2005/0651* (2013.01); *A61N 2005/0653* (2013.01); *A61N 2005/0663* (2013.01); *A61N 2005/0667* (2013.01)

(58) Field of Classification Search
CPC .... A61N 2005/0653; A61N 2005/0645; A61N 2005/0651; A61N 2005/0663
See application file for complete search history.

(56) References Cited

U.S. PATENT DOCUMENTS

| | | | |
|---|---|---|---|
| 2004/0044384 A1 | 3/2004 | Leber et al. | |
| 2006/0235346 A1* | 10/2006 | Prescott | A61N 5/0616 602/2 |
| 2007/0038273 A1 | 2/2007 | Bales et al. | |
| 2007/0167999 A1* | 7/2007 | Breden | A61N 5/06 607/88 |
| 2010/0121419 A1* | 5/2010 | Douglas | A61N 5/0616 607/90 |
| 2013/0032617 A1* | 2/2013 | Adelman | A45F 5/00 224/191 |

FOREIGN PATENT DOCUMENTS

| | | | | |
|---|---|---|---|---|
| KR | 10-2008-0094640 A | 10/2008 | | |
| KR | 10-2012-0043179 A | 5/2012 | | |
| KR | 20120043179 A * | 5/2012 | | |
| KR | 10-1181580 B1 | 9/2012 | | |
| WO | WO-2008067455 A2 * | 6/2008 | ........... | A61N 5/0601 |
| WO | WO-2010087559 A1 * | 8/2010 | ........... | A61N 5/0619 |
| WO | WO-2011158999 A1 * | 12/2011 | ........... | A61N 5/0613 |

* cited by examiner

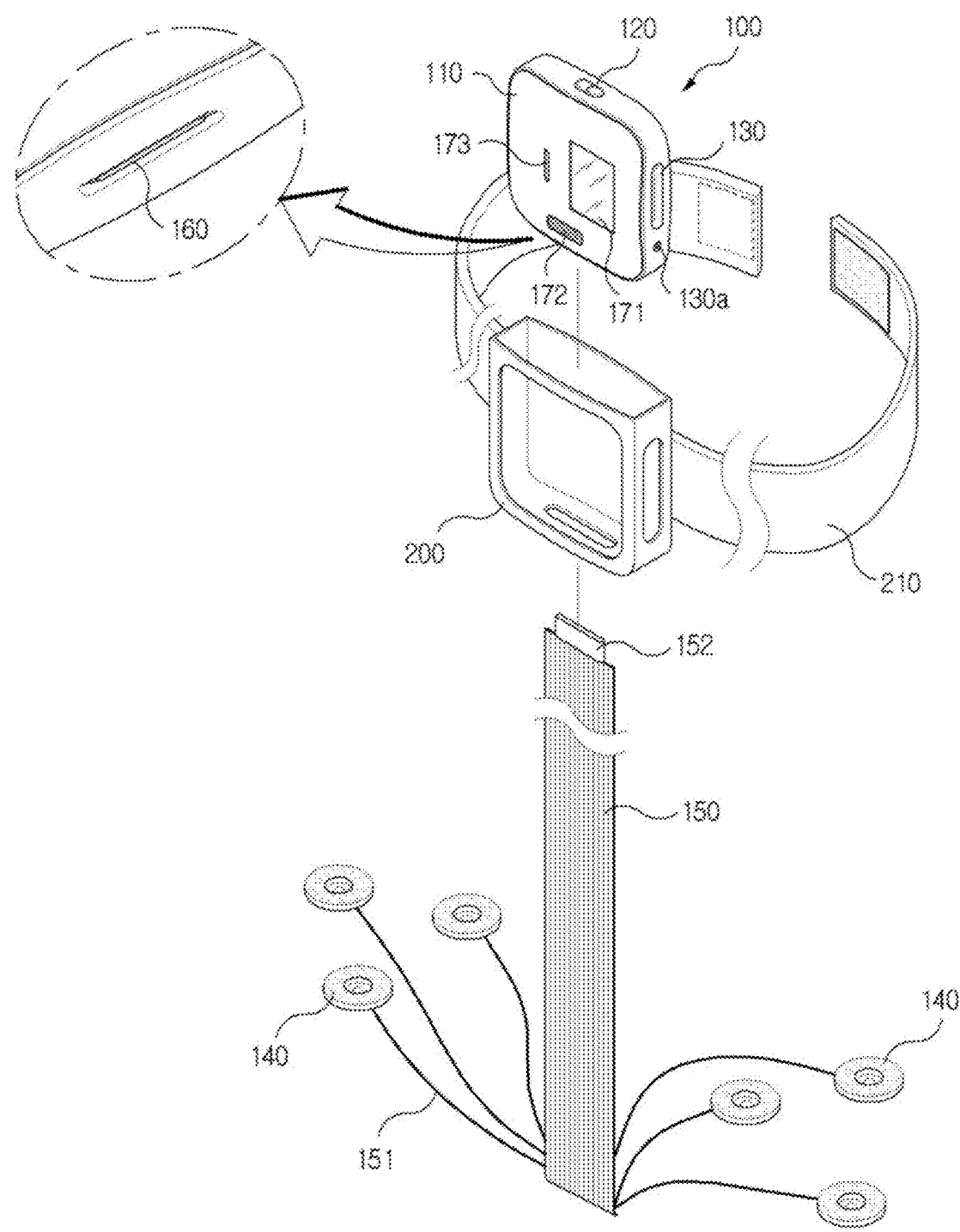
[Fig. 1]

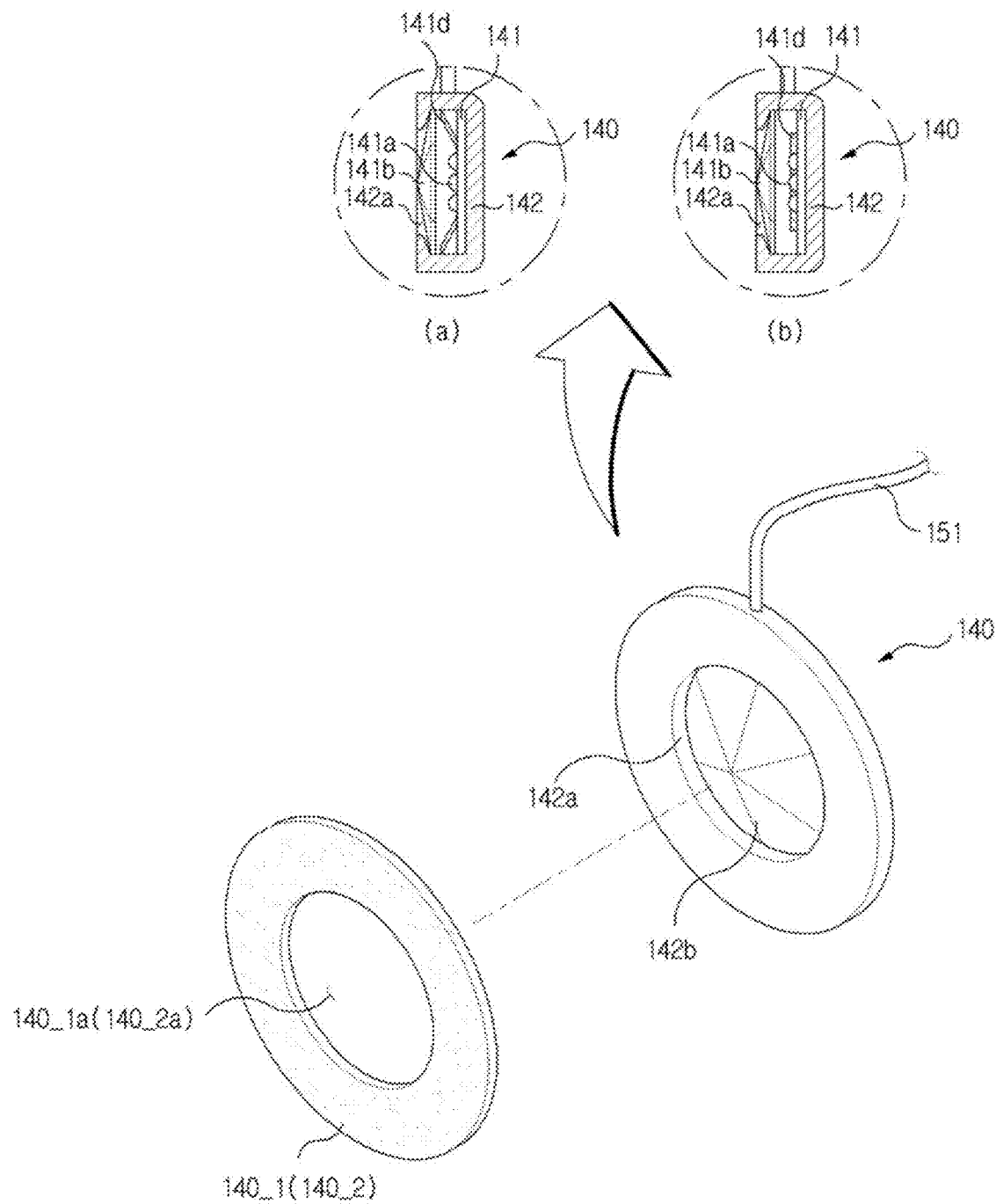
[Fig. 2]

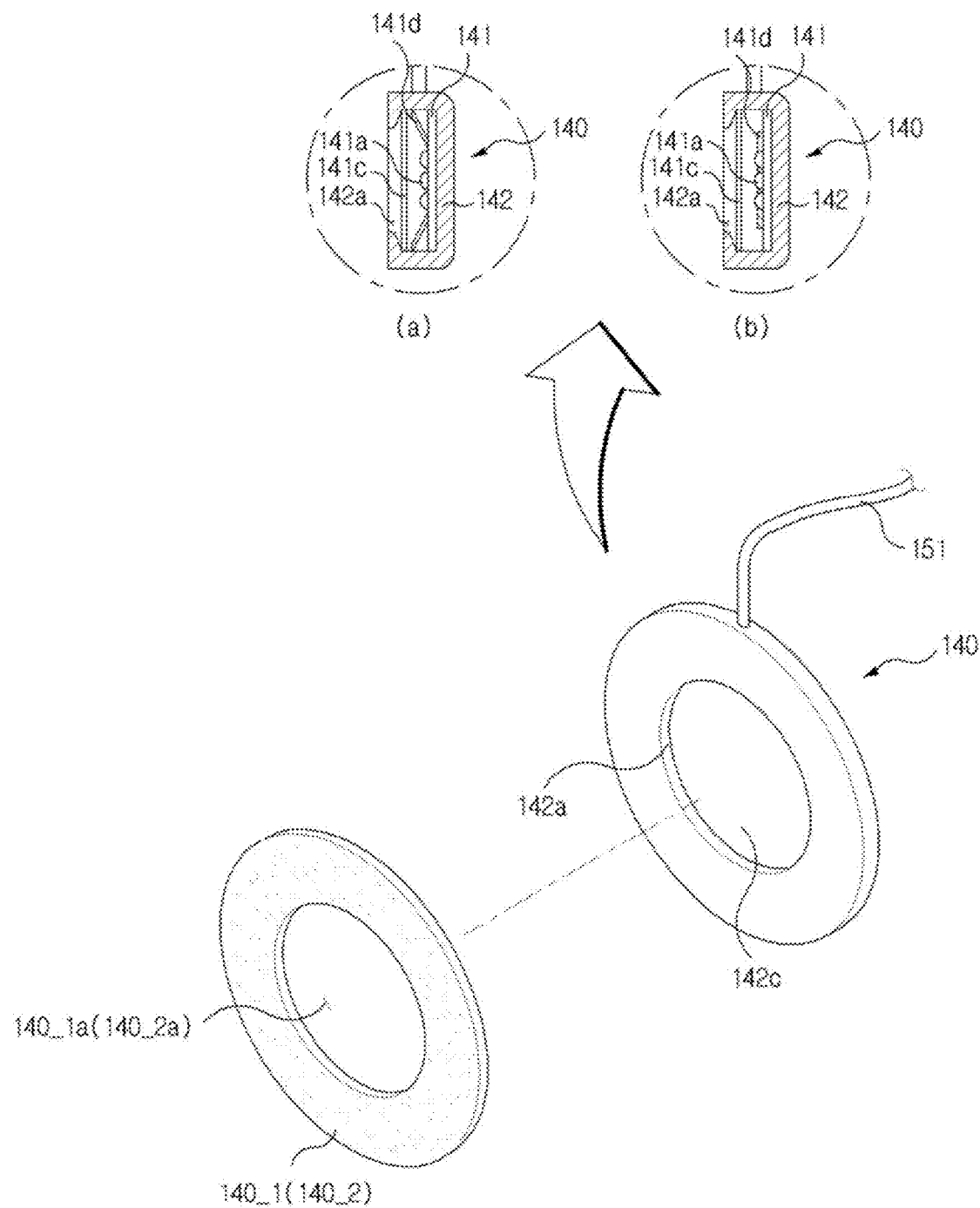
[Fig. 3]

[Fig. 4]
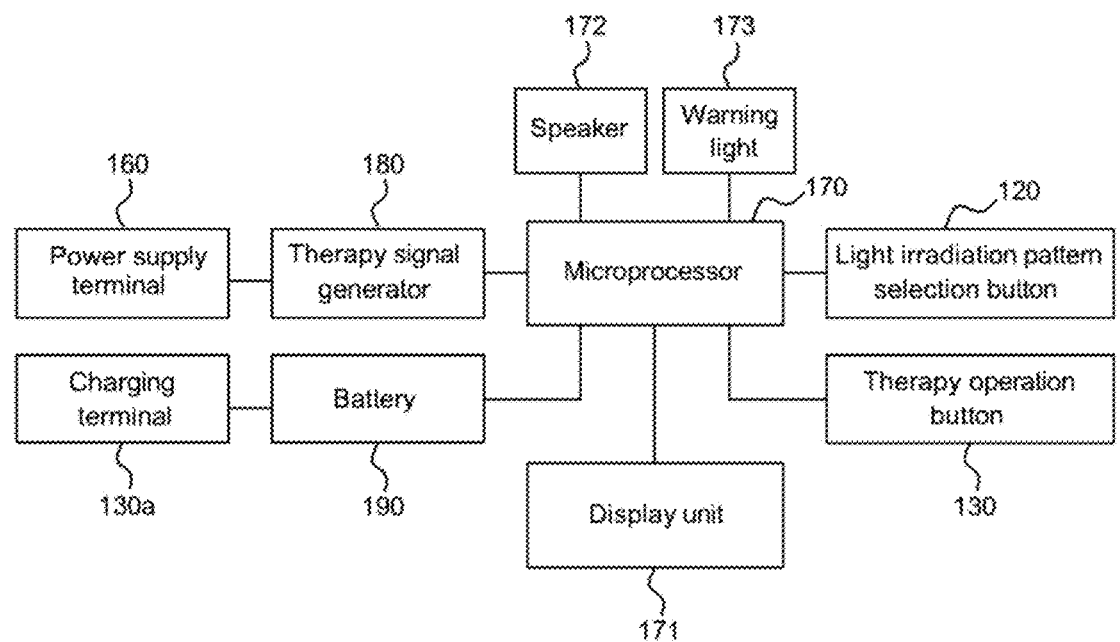

[Fig. 5]
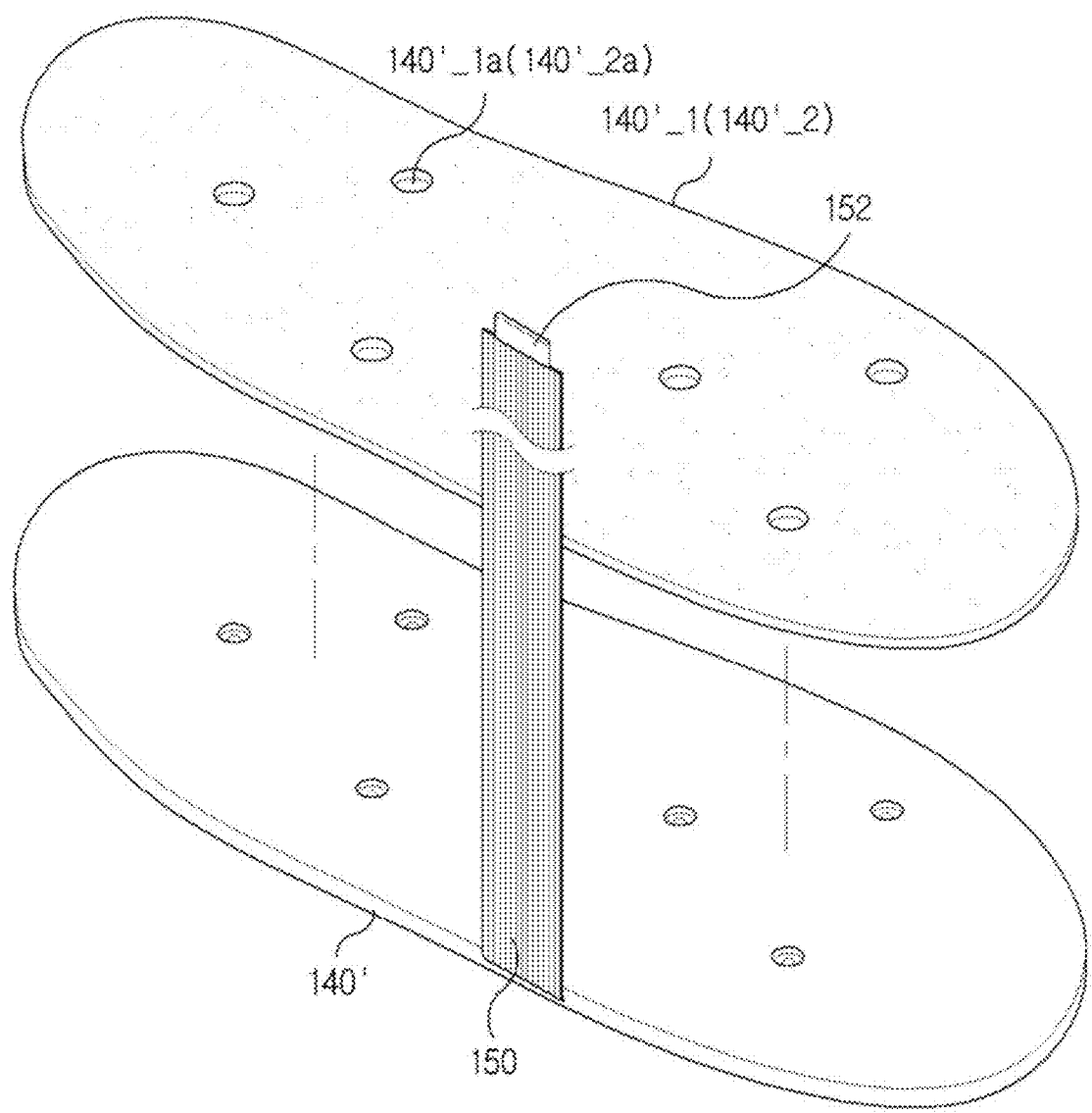

[Fig. 6]
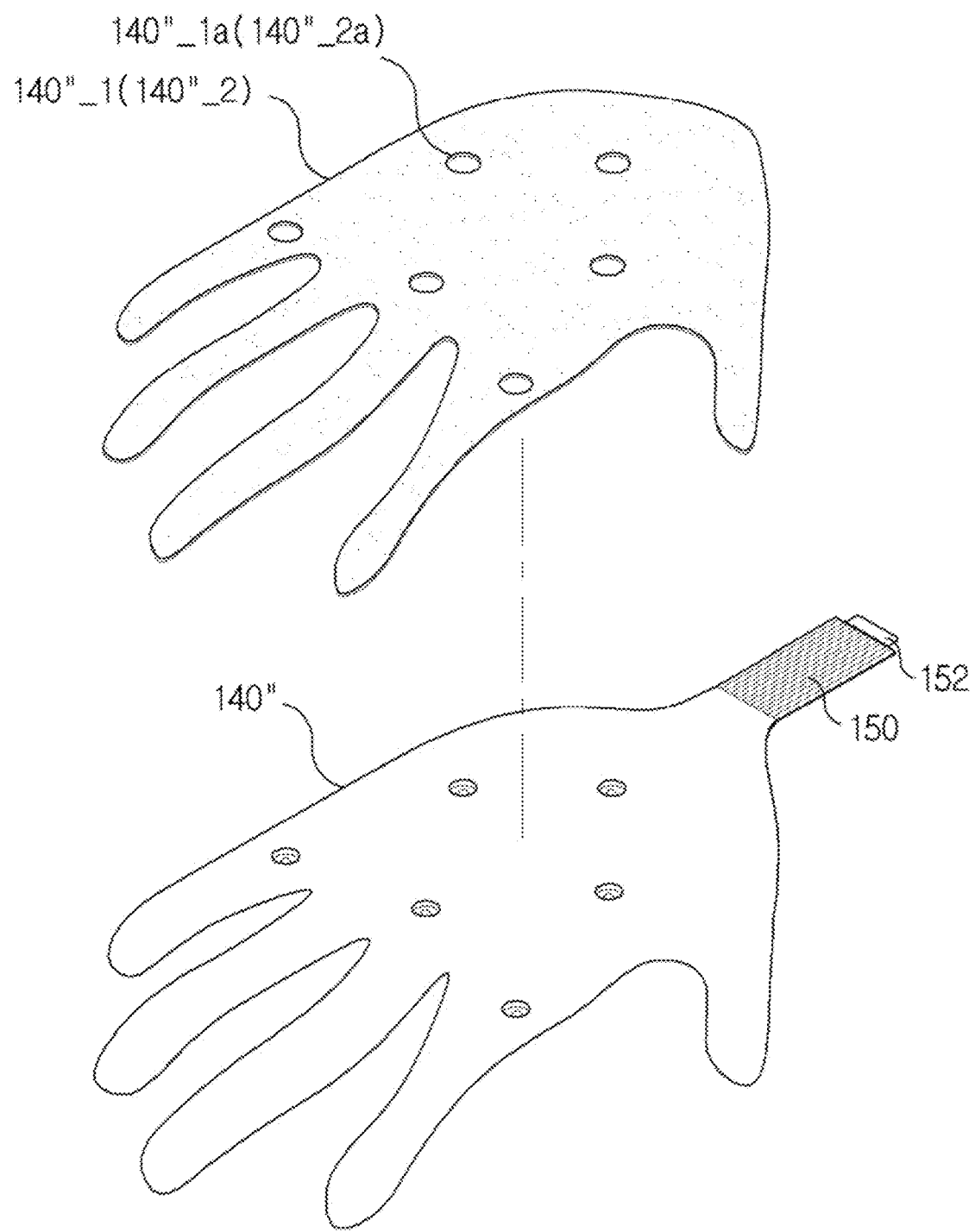

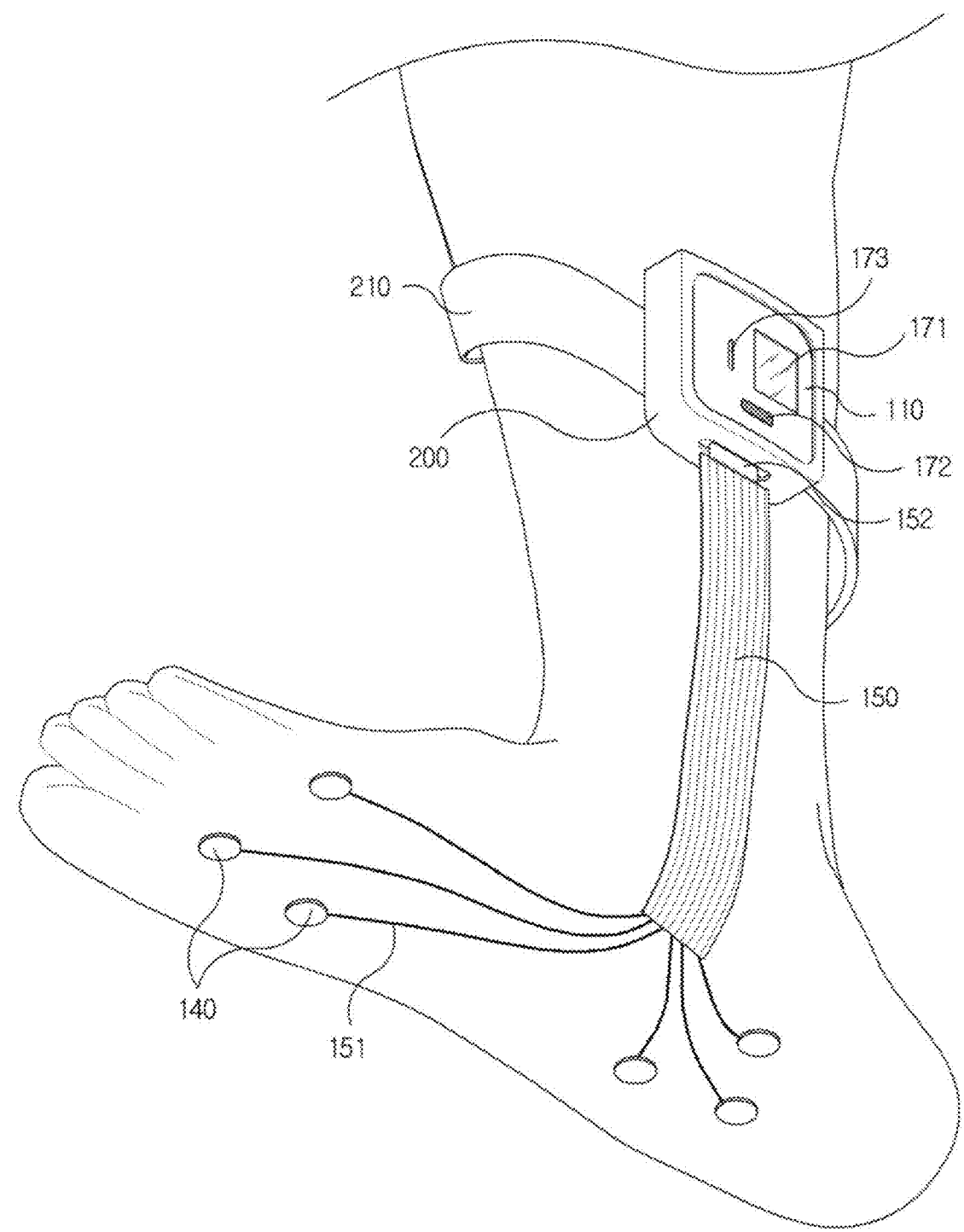
[Fig. 7]

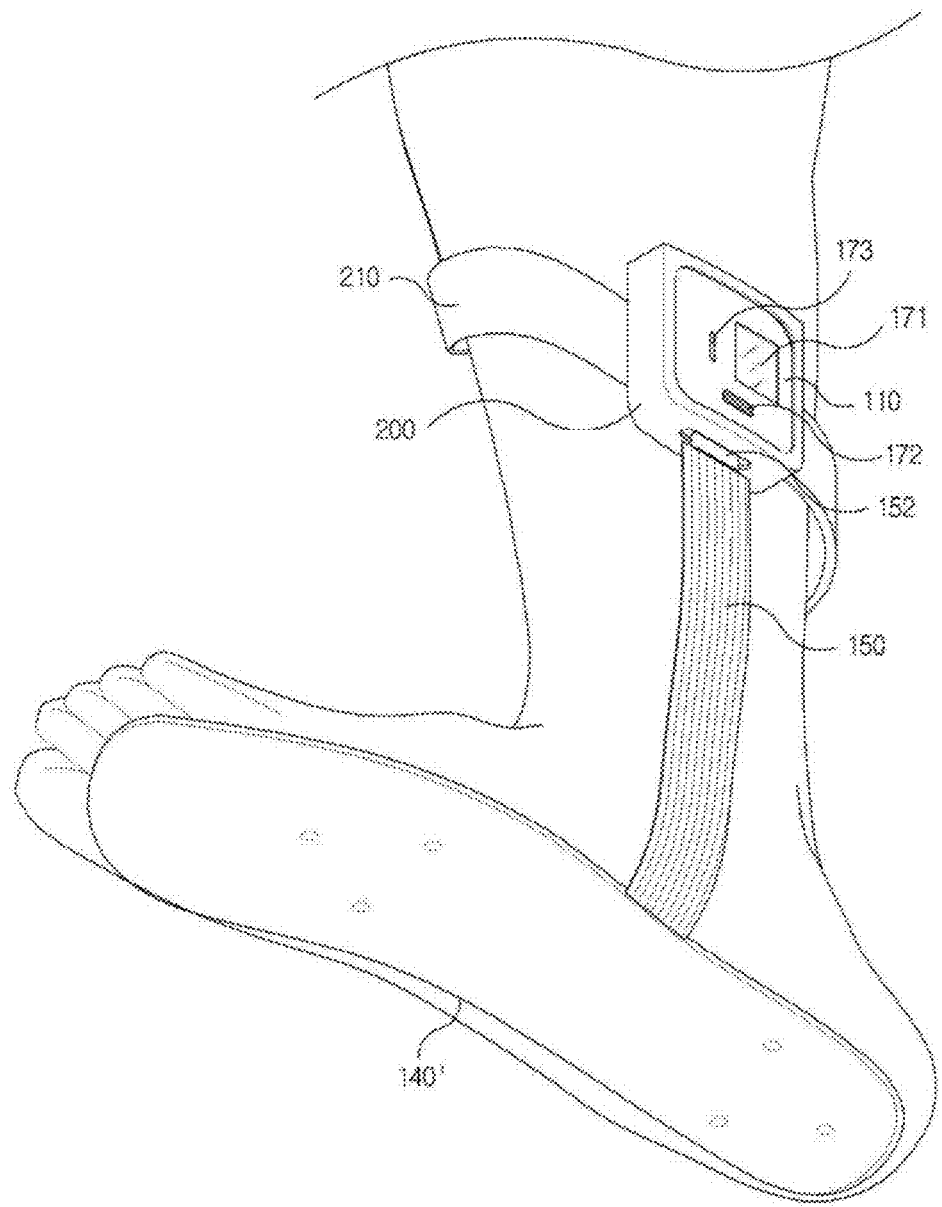
[Fig. 8]

[Fig. 9]
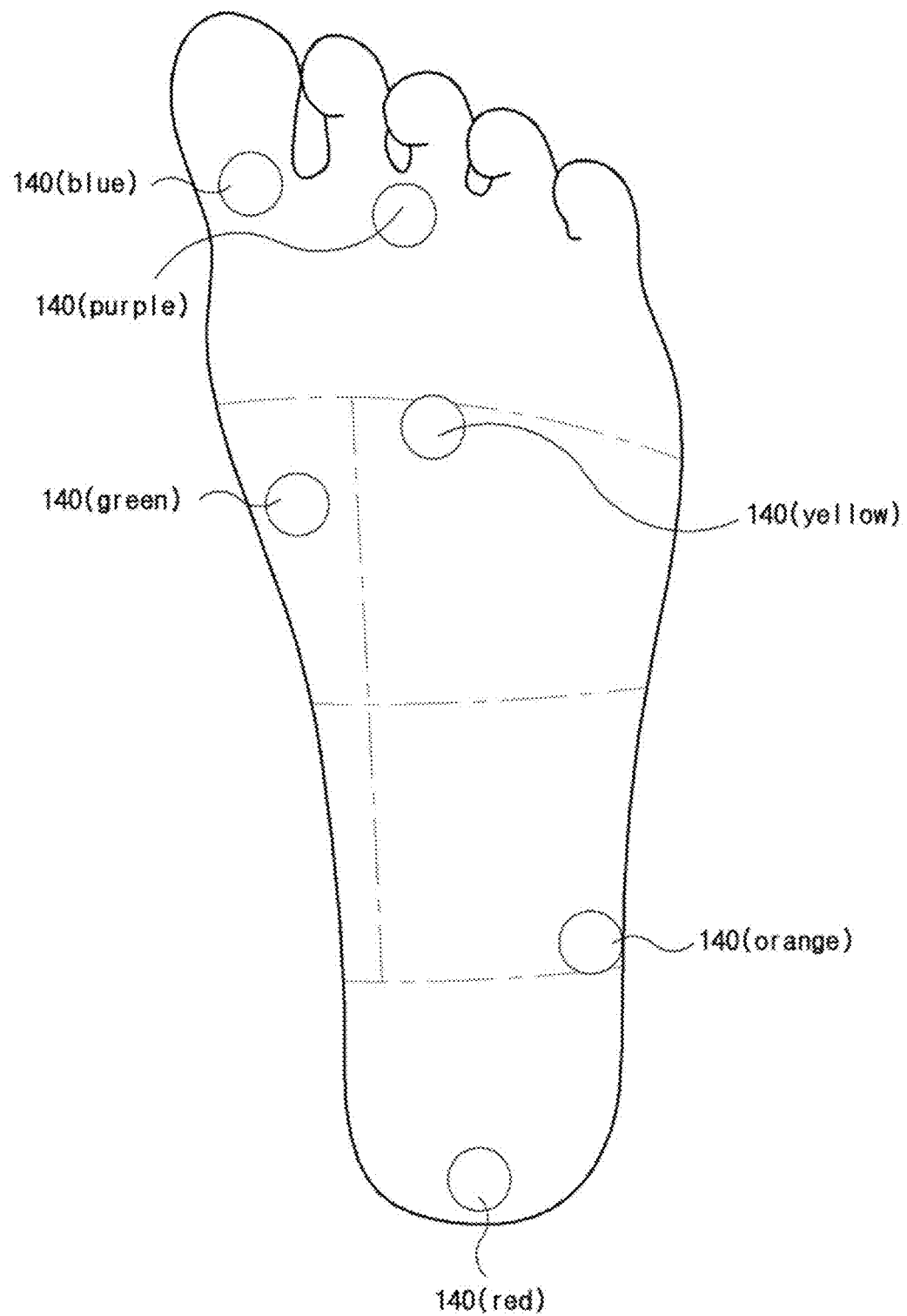

[Fig. 10]
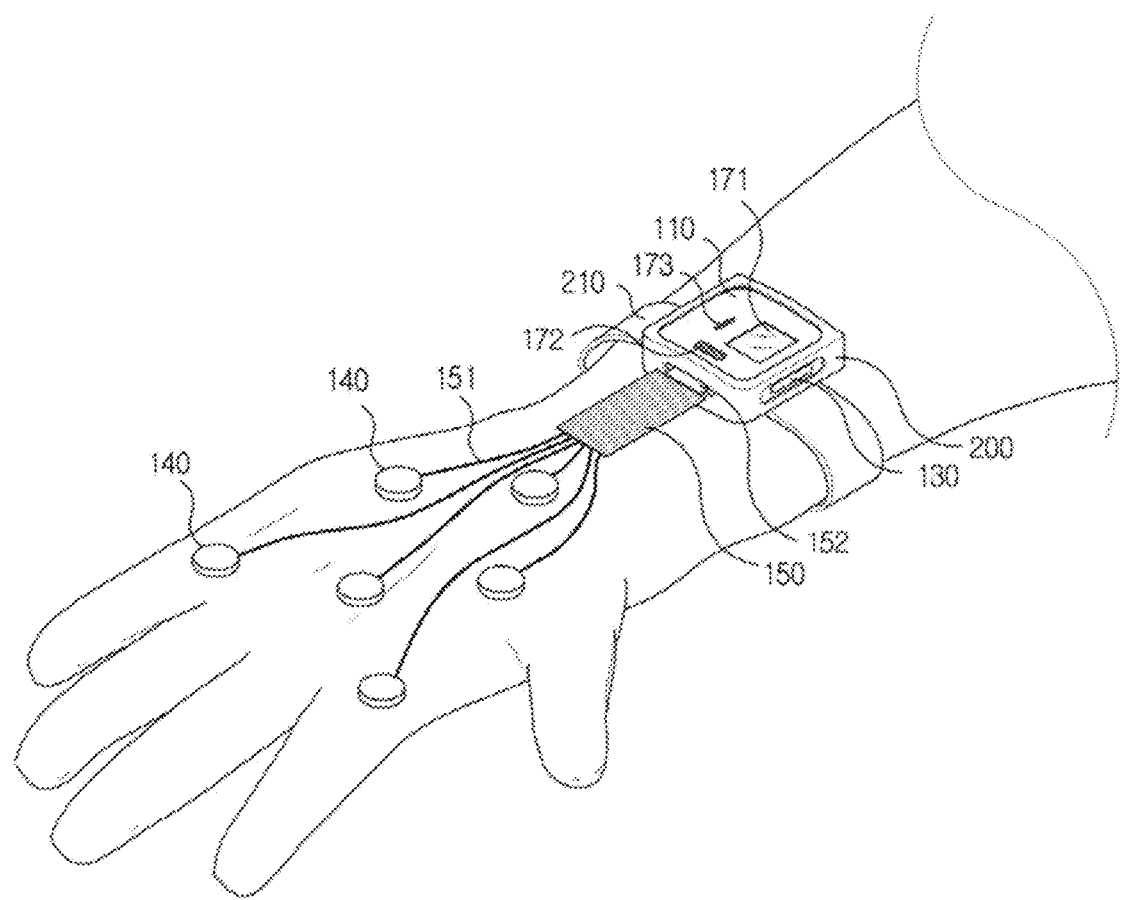

[Fig. 11]
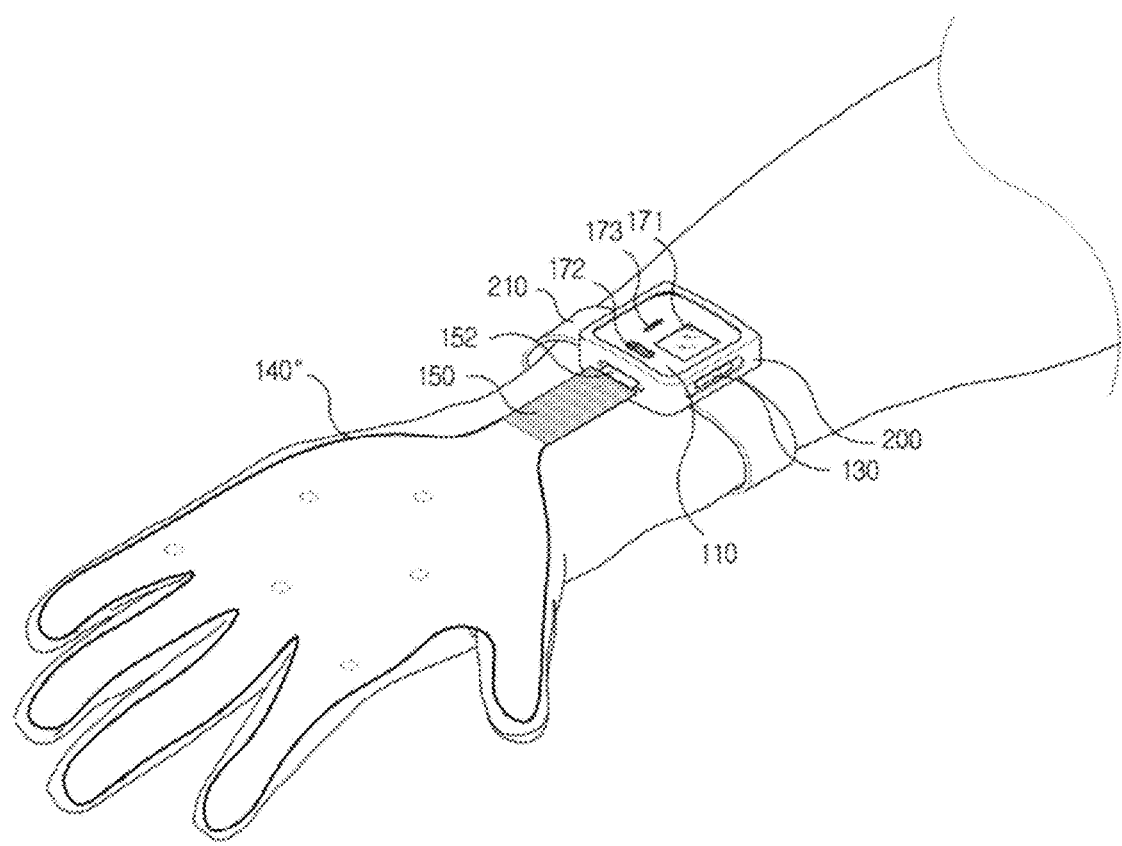

THERAPY DEVICE FOR EDEMA AND NEUROPATHY

CROSS REFERENCE TO PRIOR APPLICATIONS

This application is a National Stage Application of PCT International Patent Application No. PCT/KR2013/004208 filed on May 13, 2013, under 35 U.S.C. § 371, which is all hereby incorporated by reference in its entirety.

TECHNICAL FIELD

The present invention relates to a therapy device for edema and neuropathy and, more specifically, to a therapy device for edema and neuropathy, wherein colored light of a visible light wavelength range, which is known to be useful for treating edema and neuropathy, is irradiated to a treatment area such as acupuncture points on a foot or a hand, or the surface of the skin, that is, the edema and neuropathy treatment area of a foot or a hand.

BACKGROUND ART

Edema is an abnormal accumulation of fluid such as blood plasma, interstitial fluid and transcellular fluid, leaked from blood vessels to between cells outside of the blood vessels, in the interstitium, located beneath the skin and in the cavities of the body. The edema of cells and tissues are often caused by acute traumatic brain injury, ischemic attack and the like or chronic fluid increase such as the increase of the synovial membrane due to arthritis, hydrocephalus and glaucoma.

If this edema is not appropriately treated at an early stage, the edema could gradually cause severe damage to cells and tissues.

In order to treat this edema, it has been known to take medicines such as painkillers or use acupuncture, moxibustion, low frequency treatment, pneumatic and hydraulic massage equipment and the like so as to temporarily relieve pain or swelling. However, these methods are not effective, and thus more effective treatment methods are demanded.

For example, a diuretic is generally used in the treatment of edema, wherein the diuretic is used for the purpose of treating the edema by normalizing the extracellular fluid by reducing the renal tubule reabsorption of Na+, Cl- and water so as to increase the discharge of solute and water. However, when the diuretics are taken for a long time, it is likely to cause serious side effects such as dehydration, hypothyroidism, hyperadrenalism, congestive stroke, renal failure and the like. Therefore, the diuretics has been prescribed on a limited basis.

Neuropathy is a general term for describing a disease process that results in a functional disorder of the nervous system. In particular, neuropathy is caused by diabetes, uremia, porphyria, hypoglycemia, vitamin deficiency, vitamin B12 deficiency, sepsis, chronic liver disease and the like.

In particular, neuropathy is one of the major complications of diabetes, wherein symptomatic treatment of nerve function or treatment for preventing the gradual decline in nerve function has not been established. Therefore, the loss of sensation associated with the diabetic neuropathy is likely to be proceeded such that even minor infection can be resulted in an ulcer and more seriously the amputation. In addition, damage to the motor nerves is likely to cause the decay and muscle imbalances. However, the pathogenesis mechanisms of neuropathy have not been figured yet.

The above-mentioned diabetic neuropathy is the most common peripheral neuropathy in the western and includes neuropathy of various forms. Current treatment is only able to relieve the pain and control associated symptoms by using a painkiller or certain medicines. However, such a pain therapy using medicines has disadvantages that side effects caused by medicines frequently occur and drug tolerance can be developed due to the long term medication in the case of chronic pain, reaching a state, where the medication is not effective for relieving pain at all.

DISCLOSURE

Technical Problem

Accordingly, the present invention has been made in an effort to solve the above-mentioned problems occurring in the prior arts, and it is an objective of the present invention to provide a therapy device for edema and neuropathy, which is used, in order to treat edema or neuropathy, in the state of being attached to an edema and neuropathy treatment area of a foot or a hand by means of a double-sided adhesive tape, a hydrogel pad and the like and irradiates colored light of a visible light wavelength range emitted from a light source to the edema and neuropathy treatment area of a foot or a hand for a set time so as to relax the smooth muscles of tissues by human tissue cells having edema or neuropathy such that peripheral blood circulation and lymphatic circulation become smooth and the secretion of materials for treating edema and neuropathy (hereinafter, referred to as therapeutic materials), for example, nitrogen monoxide (NO; Nitric oxide) and cyclic Adenosine Monophosphate cAMP or cyclic Guanosine Monophospate cGMP, can be induced.

Technical Solution

To achieve the above objectives, the present invention provides a therapy device for edema and neuropathy, comprising: a case formed in a hollow container body; a light irradiation pattern selection button provided to one surface of the case and outputting any one light irradiation pattern selection signal of colored light irradiation patterns, which are divided into continuous irradiation or discontinuous irradiation; a therapy operation button provided to one surface of the case and outputting a therapy operation signal such that colored light is irradiated for a predetermined time period whenever the therapy operation button is pressed; at least one or more colored light irradiators including light sources for emitting the colored light of a visible light wavelength range to edema and neuropathy treatment areas of a foot or a hand; a power supply flat cable connected to each of the one or more colored light irradiators by one or more wires, which are divided at one end of the power supply flat cable and integrated at the other end thereof; a power supply terminal provided to one surface of the case and connected to a power connection terminal of the power supply flat cable; a microprocessor incorporated in the case and outputting a therapy start signal whenever the therapy operation signal is inputted after the light irradiation pattern selection signal is inputted and a therapy end signal after a predetermined time from the outputting of the therapy start signal; a therapy signal generator, if the therapy start signal is inputted, for outputting a therapy signal for emitting the colored light of the visible light wavelength range so as to turn on the light sources of the colored light irradiators such that the edema and neuropathy can be treated, and stopping outputting the therapy signal if the therapy end signal is inputted; and a battery for supplying power of the light irradiation pattern selection button, the therapy operation button, the colored light irradiator, the microprocessor and the therapy signal generator.

Advantageous Effects

According to the present invention, the therapeutic materials secreted from the human tissue cells, having edema or neuropathy, by the visible light enables the muscles of the human tissues and the capillaries and lymphatic capillaries, having edema or neuropathy, such that the blood flow in muscle tissues or nerve tissues, which are weakened or damaged by stresses or diseases, can be increased, activating oxygen supply and nutrient supply. As a result, the functions of the weakened or damaged muscle tissues or nerve tissues are restored, such that edema or neuropathy can be fundamentally treated.

DESCRIPTION OF DRAWINGS

FIG. 1 is a perspective view of a therapy device for edema and neuropathy according to the present invention.

FIG. 2 is a view of an embodiment for the colored light irradiator of FIG. 1.

FIG. 3 is a view of another embodiment for the colored light irradiator of FIG. 1.

FIG. 4 is a block diagram of the therapy device for edema and neuropathy according to the present invention.

FIG. 5 is a perspective view of a foot pad, to which the colored light irradiator of FIG. 1 is fixed.

FIG. 6 is a view of a hand pad, to which the colored light irradiator of FIG. 1 is fixed.

FIG. 7 is a view of an embodiment for showing a state, where the colored light irradiator according to the present invention is attached to the edema and neuropathy treatment area of the foot.

FIG. 8 is a view of another embodiment for showing a state, where the colored light irradiator according to the present invention is attached to an edema and neuropathy treatment area of a foot.

FIG. 9 is a view of an edema and neuropathy treatment area of a foot, to which the therapeutic colored light is irradiated according to the present invention.

FIG. 10 is a view of an embodiment for showing a state, where the colored light irradiator according to the present invention is attached to an edema and neuropathy treatment area of a hand, and FIG. 11 is a view of another embodiment for showing a state, where the colored light irradiator according to the present invention is attached to the edema and neuropathy treatment area of the hand.

EXPLANATION OF ESSENTIAL REFERENCE NUMERALS IN DRAWINGS

Mode for Invention

Hereinafter, the present invention will be described in more detail in connection with embodiments thereof with reference to the attached drawings.

Referring to FIG. 1 to FIG. 6, case 110 is formed in the shape of a hollow container.

A light irradiation pattern selection button 120 is provided to one surface of the case 110, and outputs a light irradiation pattern selection signal for selecting any one of light irradiation patterns, which is divided into continuous irradiation for continuously irradiating colored light for a set time (for example, 20-30 minutes) or discontinuous irradiation for discontinuously irradiating the colored light for a set time (for example, 20-30 minutes).

A therapy operation button 130 is provided to one surface of the case 110 and outputs a therapy operation signal such that the colored light is irradiated for a predetermined time period whenever the therapy operation button 130 is pressed.

At least one or more colored light irradiators 140 can be used, including light sources 141a for emitting, to edema and neuropathy treatment areas of a foot or a hand, the colored light of a visible light wavelength range, for example, orange-, red-, green-, and yellow-colored light and the like of 400 nm to 800 nm.

As shown in FIG. 1 to FIG. 3, the colored light irradiators 140 are used in a state, where the colored light irradiators 140 are attached to edema and neuropathy treatment areas of a foot or a hand by a double-sided adhesive tape 140_1 or a hydrogel pad 140_2, which is perforated with holes 140_1a, 140_2a, through which the colored light passes.

The colored light irradiators 140 are connected to a band 210, which is formed in any one shape of a VELCRO™ tape, a hook and a buckle so as to be controllable in length and wearable on a wrist or an ankle, and used as being fixed to a fixing device 200 for receiving the colored light irradiators 140. For reference, FIG. 1 illustrates the fixing device 200 connected to the band 210 in the shape of a VELCRO™ tape.

The one or more colored light irradiators 140 can be arranged in a set pattern and fixed to a foot-shaped foot pad 140' (see FIG. 5) or a hand-shaped hand pad 140" (see FIG. 6), which is connected to a below-mentioned power supply flat cable 150. As shown in FIG. 5 and FIG. 6, the foot pad 140' or the hand pad 140" is used in a state, where the foot pad 140' or the hand pad 140" is attached to a foot or a hand by a double-sided adhesive tape 140'_1, 140"_1 or a hydrogel pad 140'_2, 140"_2, which is perforated with holes 140_1'a, 140'_2a 140"_1a, 140"_2a, through which the colored light passes.

The colored light irradiator 140 includes a PCB 141 and a body part 142.

The PCB 141 is provided with at least one or more of a light emitting diode LED, an organic light emitting diode OLED, a laser diode LD or a 3-color LEDs capable of generating light in various colors as a light source 141a, which emits the colored light of a visible light wavelength range to the edema and neuropathy treatment area of a foot or a hand such that edema and neuropathy can be treated, and connected to the power supply flat cable 150 through the wires 151 so as to supply power to the light source 141a.

The body part 142 accommodates the PCB 141 therein and has a light emitting hole 142a formed in a front surface thereof so as to concentrically irradiate the therapeutic colored light to the edema and neuropathy treatment area of a foot or a hand.

As shown in expanded views (a) and (b) in FIG. 2, the colored light irradiator 140 further includes an optical filter 141b, which is provided to the body part 142 and formed of any one of plastics, glass, quartz, crystal and crystal glass, has a colored light transmitting surface formed in the shape of a circle or a polygon, for example, a pentagon, a hexagon, an octagon and the like, through cutting or formed in a flat plate or a convex lens, and filters and focuses the colored light, emitted from the light source 141a, so as to emit the same through the light emitting hole 142a. For reference, the LED illumination such as the LED, the OLED, the LD, the 3-color LED and the like is theoretically a single-wavelength illumination, but has a wide frequency spectral width in reality so as to have a wide bandwidth rather than a single-wavelength. In order to obtain single frequency spectral components, the optical filter 141b having frequency characteristics similar to a desired single frequency is used in the LED illumination such that part of the light emitted from the LED illumination is resonantly absorbed and the optical filter 141b selects and emits the light having the frequency components which the optical filter 141b originally has.

As shown in expanded views (a) and (b) in FIG. 3, the colored light irradiator 140 further includes an optical filter 141c, which is provided to the body part 142 and formed of a transparent carbon nanotube film so as to additionally generate heat by the colored light of the visible light wavelength range, emitted from the light source 141a. For reference, if the optical filter 141c formed of such a carbon nanotube film is used so as to apply low heat, which does not induce burns on the edema and neuropathy treatment area of a foot or a hand, then the blood flow of the treatment area can be increased.

As shown in expanded views (a) and (b) in FIG. 2 and expanded views (a) and (b) in FIG. 3, the colored light irradiator 140 further includes a reflection body 141d, which is provided in the periphery of the light source 141a, provided to the PCB 141 accommodated in the body part 142, and formed of any one of a reflection plate or a reflection film, so as to reflect the colored light, emitted from the light source 141a, towards the light emitting hole 142a.

It is preferable that the body part 142 of the colored light irradiator 140 is formed in the shape of a patch by using any one of cotton, rubber, PVC, silicon and urethane. Even though FIG. 1 to FIG. 3 illustrate a circular patch, it is possible to modify the patch in various shapes such as a square, a rectangle, an oval and the like in accordance with circumstances.

The power supply flat cable 150 is connected to each of the one or more colored light irradiators 140 by one or more wires 151, which are divided at one end of the power supply flat cable 150 and integrated at the other end thereof.

A power supply terminal 160 is provided to one surface of the case 110 and connected to a power connection terminal 152 of the power supply flat cable 150.

A microprocessor 170 is incorporated in the case 110 and outputs a therapy start signal whenever the therapy operation signal is inputted after the inputting of the light irradiation pattern selection signal, and a therapy end signal after a predetermined time from the outputting of the therapy start signal.

The microprocessor 170 enables a display unit 171, which is provided to one surface of the case 110 and operates by the power of a battery 190, to display a remaining time to irradiate the colored light until the therapy end signal is outputted after the outputting of the therapy start signal, or a remaining power state of the battery 190.

The display unit 171 may include an LCD or one or more LEDs and can display the remaining colored light irradiation time, the remaining power amount and the like.

The microprocessor 170 enables a speaker 172, which is provided to one surface of the case 110 and operates by the power of the battery 190, to output an alarm sound or a voice message informing of therapy start or therapy end, while outputting the therapy start signal or the therapy end signal.

The microprocessor 170 turns on a warning light 173, which is provided to one surface of the case 110 and operates by the power of the battery 190, or make the warning light 173 flicker until the therapy end signal is outputted after the outputting of the therapy start signal, so as to indicate an colored light irradiation operation state.

If the therapy start signal is inputted, a therapy signal generator 180 outputs a therapy signal for emitting the colored light of the visible light wavelength range so as to turn on the light sources 141a of the colored light irradiators 140 such that edema and neuropathy can be treated, and stops outputting the therapy signal if the therapy end signal is inputted.

The battery 190 supplies power of the light irradiation pattern selection button 120, the therapy operation button 130, the colored light irradiator 140, the microprocessor 170 and the therapy signal generator 180.

The battery 190 is to be a disposable battery or a re-chargeable battery, wherein the re-chargeable battery is supplied with power to be charged through a charging adapter, which is connected to a charging terminal 130a provided to one surface of the case 110.

For reference, FIG. 1 illustrates an insertion charging method as a battery charging method, wherein the charging adapter is inserted into the charging terminal 130a so as to be connected to each other. However, it is also possible to realize a contact-charging method of connecting the charging terminal to a charger through mutual contact and any other various wireless charging methods using electromagnetic Induction action, magnetic resonance, electric field resonance, microwave and the like.

A therapy device for edema and neuropathy 100 structured as above according to the present invention is used as follows.

The therapy device for edema and neuropathy 100 according to the present invention is based on the photo-activated modulation of smooth muscle PAMS and to be attached to a treatment area such as the acupuncture points of a foot or a hand or the surface of the skin, that is, an edema and neuropathy treatment area of a foot or a hand so as to irradiate low level visible light known to be useful for treating edema and neuropathy.

A user attaches the colored light irradiators 140 of the therapy device for edema and neuropathy 100 to the acupuncture points of a foot or a hand or the surface of the skin, known to be useful for treating edema and neuropath, and irradiates the low level visible light for a predetermined time, for example, 20-30 minutes according to the symptoms of the user so as to induce the secretion of the therapeutic materials such as nitrogen monoxide (NO; Nitric oxide) and cyclic Adenosine Monophosphate cAMP or cyclic Guanosine Monophospate cGMP, by the human tissue cells having edema or neuropathy. The therapeutic materials secreted by the human tissue cells having edema or neuropathy by the visible light stimulation enables the smooth muscles of the human tissues having edema or neuropathy to relax, such that the blood flow in muscle tissues or nerve tissues, which are weakened or damaged by stresses or diseases, can be increased, activating oxygen supply and nutrient supply. Further, the functions of the weakened or damaged muscle tissues or nerve tissues are restored through the increase of cellular tissue metabolism, such that edema or neuropathy can be fundamentally treated.

For example, FIG. 7 is a view of an embodiment for showing a state, where the colored light irradiators 140 according to the present invention are attached to an edema and neuropathy treatment area of a foot, and FIG. 8 is a view of another embodiment for showing a state, where the colored light irradiators 140 according to the present invention is attached to an edema and neuropathy treatment area of a foot.

Referring to FIG. 7, the user attaches the double-sided adhesive tape 140_1 or the hydrogel pad 140_2 and the like, which are perforated with the holes 140_1a, 140_2a, through which the colored light passes, to at least one or more (for example, 6) colored light irradiators 140 and brings the body parts 142 to a treatment area such that the therapeutic colored light can be concentrically irradiated to the edema and neuropathy treatment area of the foot through the light emitting holes 142a of the body parts 142.

Referring to FIG. 8, the user attaches the double-sided adhesive tape 140'_1 or the hydrogel pad 140'_2 and the like, which are perforated with the holes 140_1'a, 140'_2a, through which the colored light passes, to the foot pad 140', on which at least one or more (for example, 6) colored light irradiators 140 are fixed, and brings the foot pad 140' to the foot such that the therapeutic colored light can be concentrically irradiated to the edema and neuropathy treatment area of the foot through the light emitting holes 142a of the body parts 142.

For reference, FIG. 9 is a view of an edema and neuropathy treatment area of a foot, to which the therapeutic colored light is irradiated according to the present invention, wherein, for example, one of the colored light irradiators 140 is attached to the lower part of a big toe among a lot of acupuncture points of the sole of the foot so as to irradiate blue-colored light thereto, another one of the colored light irradiators 140 is attached to between the lower parts of second and third toes so as to irradiate purple-colored light thereto, further colored light irradiators 140 are attached to the arch of the sole so as to irradiate yellow- and green-colored light thereto, and the remaining colored light irradiators 140 to the heel and the outside of the heel so as to irradiate red- and orange-colored light thereto.

For example, FIG. 10 is a view of an embodiment for showing a state, where the colored light irradiator according to the present invention is attached to an edema and neuropathy treatment area of a hand, and FIG. 11 is a view of another embodiment for showing a state, where the colored light irradiator according to the present invention is attached to the edema and neuropathy treatment area of the hand.

Referring to FIG. 10, the user attaches the double-sided adhesive tape 140_1 or the hydrogel pad 140_2 and the like, which are perforated with the holes 140_1a, 140_2a, through which the colored light passes, to at least one or more (for example, 6) colored light irradiators 140 and brings the body parts 142 to a treatment area such that the therapeutic colored light can be concentrically irradiated to an edema and neuropathy treatment area of a hand (for example, Taeyeon, Daereung or Shinmun known as the acupuncture points on the palm side and Yanggye, Yangji or Yanggok known as the acupuncture points on the back side of a hand, and the like) through the light emitting holes 142a of the body parts 142.

Referring to FIG. 11, the user attaches the double-sided adhesive tape 140"_1 or the hydrogel pad 140"_2 and the like, which are perforated with the holes 140_1"a, 140"_2a, through which the colored light passes, to the hand pad 140", on which at least one or more (for example, 6) colored light irradiators 140 are fixed, and brings the hand pad 142" to the treatment area such that the therapeutic colored light can be concentrically irradiated to the edema and neuropathy treatment area of the hand (for example, Taeyeon, Daereung or Shinmun known as the acupuncture points on the palm side and Yanggye, Yangji or Yanggok known as the acupuncture points on the back side of a hand, and the like) through the light emitting holes 142a of the body parts 142.

In the state, where the body part 142 of the colored light irradiators 140 are attached to the edema and neuropathy treatment area of the hand, or the foot pad 140' or hand pad 140" is attached to the foot or the hand, as described above, if the user operates the light irradiation pattern selection button 120 so as to select any one of the colored light irradiation patterns, which are divided into the continuous irradiation and the discontinuous irradiation, and presses the therapy operation button 130, then the therapy operation button 130 outputs the therapy operation signal.

Subsequently, as this therapy operation signal is inputted to the microprocessor 170, the microprocessor 170 outputs the therapy start signal for a set time (for example, 20-30 minutes). In response thereto, the therapy signal generator 180 outputs the therapy signal for emitting the colored light of the visible light wavelength range in order to treat edema and neuropathy such that the light sources 141a of the colored light irradiator 140 are turned on. If the microprocessor 170 automatically outputs the therapy end signal after the set time, the therapy signal generator 180 also stops outputting the therapy signal such that the light sources 141a are turned off.

As the light sources 141a are turned on, the therapeutic colored light to be emitted through the light emitting holes 142a of the body parts 142 are concentrically irradiated from this time point to the edema and neuropathy treatment area for the set time (for example, 20-30 minutes).

Meanwhile, while the light sources 141a are turned on as described above, if the user presses the therapy operation button 130 such that the therapy operation button 130 outputs the therapy operation signal to be inputted to the microprocessor 170, the microprocessor 170 immediately outputs the therapy end signal so as to turn off the light sources 141a in the middle of outputting the therapy start signal. Accordingly, the user can finish the therapy whenever he wants by pressing the therapy operation button 130 in the middle of the edema and neuropathy treatment using the colored light.

Meanwhile, the microprocessor 170 can inform the user of the remaining time to irradiate the colored light until the therapy end signal is outputted after the outputting of the therapy start signal or the remaining power state of the battery 190 through the display unit 171 provided to one surface of the case 110. Further, the microprocessor 170 can inform the user of the therapy start and therapy end through the speaker 172 by outputting an alarm sound or a voice message. Furthermore, the microprocessor 170 can inform the user of a colored light irradiation operation state by turning on the warning light 173 or making the warming light 173 flicker.

The therapy term using the therapy device for edema and neuropathy 100 according to the present invention, operating as described above, is appropriately to be 1 week to 4 weeks even though there may be some individual differences according to the degree of edema and neuropathy.

For example, it is preferable that the visible light is irradiated to an edema and neuropathy treatment area of a foot or a hand for 20-30 minutes every day for the first week and then the visible light is irradiated to the edema and neuropathy treatment area of a foot or a hand for 20-30 minutes every other day for the next three weeks such that the secretion of the therapeutic materials such as nitrogen monoxide (NO; Nitric oxide) and cyclic Adenosine Monophosphate cAMP or cyclic Guanosine Monophospate cGMP, by the human tissue cells having edema or neuropathy can be induced.

As described above, while the present invention has been particularly shown and described with reference to the example embodiments thereof, it will be understood by those of ordinary skill in the art that the above embodiments of the present invention are all exemplified and various changes, modifications and equivalents may be made therein without changing the essential characteristics and scope of the present invention defined by the following claims.

The invention claimed is:

1. A therapy device for edema and neuropathy in a foot or a hand, comprising:
    a fixing device (200) connected to a band (210), the fixing device having a hollow shape;
    a case (110) configured to be inserted into the fixing device, wherein the case is removable from the fixing device;
    a light irradiation pattern selection button (120) provided to one surface of the case (110) and outputting any one light irradiation pattern selection signal of colored light irradiation patterns, which are divided into continuous irradiation or discontinuous irradiation;
    a therapy operation button (130) provided to one surface of the case (110) and outputting a therapy operation signal such that colored light is irradiated for a predetermined time period whenever the therapy operation button (130) is pressed;
    at least one or more colored light irradiators (140) including light sources (141a) for emitting the colored light of a visible light wavelength range to edema and neuropathy treatment areas of a foot or a hand,
    wherein each colored light irradiator includes a printed circuit board (PCB) (141) and a body part (142) for accommodating the PCB,
    wherein the body part of the each colored light irradiator is formed in a shape of a patch made by any one of cotton, rubber, PVC, silicon and urethane;
    a power supply flat cable (150) connected to each of the one or more colored light irradiators (140) by one or more wires (151), which are divided at one end of the power supply flat cable (150) and integrated at the other end thereof;
    a power supply terminal (160) provided to one surface of the case (110) and connected to a power connection terminal (152) of the power supply flat cable (150);
    wherein each colored light irradiator (140) is connected to each wire (151), the each wire connected to one end of the power supply flat cable (150), the other end of the power supply flat cable connected to one end of the power connection terminal (152), the other end of the power connection terminal connected to the power supply terminal (160) via a perforated hole of the fixing device,
    a microprocessor (170) incorporated in the case (110) and outputting a therapy start signal whenever the therapy operation signal is inputted after the inputting of the light irradiation pattern selection signal and a therapy end signal after a predetermined time from the outputting of the therapy start signal;
    a therapy signal generator (180), if the therapy start signal is inputted, for outputting a therapy signal for emitting the colored light of the visible light wavelength range so as to turn on the light sources (141a) of the colored light irradiators (140) such that edema and neuropathy are treated, and stopping outputting the therapy signal if the therapy end signal is inputted; and
    a battery (190) for supplying power of the light irradiation pattern selection button (120), the therapy operation button (130), the colored light irradiator (140), the microprocessor (170) and the therapy signal generator (180),
    wherein the one or more colored light irradiators (140) is arranged in a set pattern and fixed to a foot-shaped foot pad (140') or a hand-shaped hand pad (140"), which is connected to the power supply flat cable (150), and the foot pad (140') or the hand pad (140") is used in a state, where the foot pad (140') or the hand pad (140") is attached to a foot or a hand by a double-sided adhesive tape (140'_1, 140"_1) or a hydrogel pad (140'_2, 140"_2), which is perforated with colored light passing holes (140_1'a, 140'_2a) or (140"_1a, 140"_2a).

2. The therapy device according to claim 1, wherein the one or more colored light irradiators is used in a state, where the one or more colored light irradiators is attached to an edema and neuropathy treatment area of a foot or a hand by a double-sided adhesive tape (140_1) or a hydrogel pad (140_2) which is perforated with the colored light passing holes (140_1a, 140_2a).

3. The therapy device according to claim 1,
    wherein the printed circuit board (PCB) (141) is provided with at least one or more of a light emitting diode (LED), an organic light emitting diode (OLED), a laser diode (LD) or a 3-color LED capable of generating light in various colors as a light source (141a), which emits the colored light of the visible light wavelength range to the edema and neuropathy treatment area of a foot or a hand such that edema and neuropathy are treated, and connected to the power supply flat cable (150) through the wires (151) so as to supply power to the light source (141a),
    wherein the body part (142) has a light emitting hole (142a) formed in a front surface thereof so as to concentrically irradiate the therapeutic colored light to the edema and neuropathy treatment area of a foot or a hand.

4. The therapy device according to claim 3, wherein the colored light irradiator (140) further includes an optical filter (141b), which is provided to the body part (142) and formed of any one of plastics, glass, quartz, crystal and crystal glass, has a colored light transmitting surface formed in the shape of a circle or a polygon through cutting or formed in a flat plate or a convex lens, and filters and focuses the colored light, emitted from the light source (141a), so as to emit the same through the light emitting hole (142a).

5. The therapy device according to claim 3, wherein the colored light irradiator (140) further includes an optical filter (141c), which is provided to the body part (142) and formed of a transparent carbon nanotube film so as to additionally generate heat by the colored light of the visible light wavelength range, emitted from the light source (141a).

6. The therapy device according to claim 3, wherein the colored light irradiator (140) further includes a reflection body (141d), which is provided in the periphery of the light source (141a), provided to the PCB (141) accommodated in the body part (142), and formed of any one of a reflection plate or a reflection film, so as to reflect the colored light, emitted from the light source (141a), towards the light emitting hole (142a).

7. The therapy device for according to claim 1, wherein the microprocessor (170) enables a display unit (171), which is provided to one surface of the case (110) and operates by the power of a battery (190), to display a remaining time to irradiate the colored light until the therapy end signal is outputted after the outputting of the therapy start signal or a remaining power state of the battery (190).

8. The therapy device according to claim 1, wherein the microprocessor (170) enables a speaker (172), which is provided to one surface of the case (110) and operates by the power of the battery (190), to output an alarm sound or a voice message informing of therapy start or therapy end, while outputting the therapy start signal or the therapy end signal.

9. The therapy device according to claim 1, wherein the microprocessor (170) turns on a warning light (173), which is provided to one surface of the case (110) and operates by the power of the battery (190), or make the warning light (173) flicker until the therapy end signal is outputted after the outputting of the therapy start signal, so as to indicate a colored light irradiation operation state.

10. The therapy device according to claim 1, wherein the battery (190) is to be a disposable battery or a re-chargeable battery, and the re-chargeable battery is supplied with power to be charged through a charging adapter, which is connected to a charging terminal (130*a*) provided to one surface of the case (110).

* * * * *